United States Patent [19]

Voigt et al.

[11] Patent Number: 4,898,645

[45] Date of Patent: Feb. 6, 1990

[54] PROCESS FOR THE PRODUCTION OF PURE TETRAFLUOROETHYLENE

[75] Inventors: Hartmut Voigt, Winhöring; Reinhold Freudenreich, Burgkirchen, both of Fed. Rep. of Germany

[73] Assignee: Hoechst Aktiengesellschaft, Frankfurt am Main, Fed. Rep. of Germany

[21] Appl. No.: 238,546

[22] Filed: Aug. 30, 1988

[30] Foreign Application Priority Data

Sep. 1, 1987 [DE] Fed. Rep. of Germany ....... 3729106

[51] Int. Cl.$^4$ .......................... B01D 3/34; C07C 17/38
[52] U.S. Cl. ........................................ 203/67; 203/73; 570/136; 570/153; 570/178
[58] Field of Search ........................ 203/67, 71, 73, 78, 203/84, 98; 570/134, 136, 153, 178

[56] References Cited

U.S. PATENT DOCUMENTS

| | | | |
|---|---|---|---|
| 2,406,794 | 9/1946 | Benning et al. | 570/178 |
| 3,101,304 | 8/1963 | Wiist | 203/67 |
| 3,152,051 | 10/1964 | Fainberg et al. | 570/178 |
| 3,282,801 | 11/1966 | Wiist | 203/62 |

FOREIGN PATENT DOCUMENTS 0038970 4/1983 European Pat. Off. .

*Primary Examiner*—Wilbur Bascomb

[57] ABSTRACT

A process is described for the production of pure tetrafluoroethylene from a gas formed in the pyrolysis of a fluorocarbon compound having 1 to 4 carbon atoms, which can contain a hydrogen atom and a chlorine atom. The pyrolysis gas, after hydrogen chloride or hydrogen fluoride and also if necessary steam have been separated off, is condensed under pressure and distilled in a plurality of columns, in the first column the low boilers being distilled off, preferably with a reflux ratio of 6 to 15 kg per kg of tetrafluoroethylene produced, and in the second column tetrafluoroethylene, preferably with a reflux ratio of 3 to 5 kg per kg of tetrafluoroethylene produced. Per kg of tetrafluoroethylene produced, from 0.6 to 2 kg of difluoromonochloromethane are fed into the second column as a distillation aid. The novel process makes it possible to produce pure tetrafluoroethylene at comparatively reduced energy and apparatus costs.

8 Claims, No Drawings

PROCESS FOR THE PRODUCTION OF PURE TETRAFLUOROETHYLENE

DESCRIPTION

The invention relates to a process for the production of pure tetrafluoroethylene from a gas formed by pyrolysis of a fluorocarbon compound having 1 to 4 carbon atoms, which can contain a hydrogen and a chlorine atom.

Tetrafluoroethylene is produced on an industrial scale by pyrolysis of fluorocarbon compounds, generally in the range from 400° to 1,000° C. For this purpose, the fluorocarbon compounds which are frequently used are those having 1 to 4 carbon atoms and also containing an H atom and a Cl or Br atom in addition to C and F atoms. The gas mixture formed in the pyrolysis is usually freed of eliminated HF, HCl or HBr by washing with water or an aqueous solution of the substances mentioned, the gas stream is dried and condensed. This procedure liquefies tetrafluoroethylene (hereinafter designated as TFE), unconverted starting material and undesired by-products, while nitrogen, carbon oxide and, corresponding to its partial pressure, also some TFE, other pyrolysis products and also pyrolysis starting material remain as gases. The liquefied product is then worked up by distillation, the compounds and azeotropic mixtures whose boiling points under the conditions chosen are lower than the boiling point of TFE, which therefore boil at a lower temperature than TFE (hereinafter also called "low-boiling compounds") being distilled off at the top in a first column. The bottom product of this first column is then usually distilled in a second column from which more or less pure TFE is distilled off at the top, while at the bottom of this column the compounds and azeotropic mixtures remain whose boiling points under the conditions chosen are higher than the boiling point of TFE, which therefore boil at a higher temperature than TFE (hereinafter also called "high-boiling components"). The high-boiling components, possibly also the low-boiling components, are then further worked up by distillation, in particular in order to recover the uncoverted pyrolysis starting material as pure as possible and recycle it into the pyrolysis.

The boiling behavior of the various compounds and azeotropic mixtures contained in the liquid pyrolysis gas condensate in addition to TFE has an adverse effect on the preparation of the TFE in pure form and renders it expensive in terms of apparatus and energy required. Of the various processes known to improve the workup of the pyrolysis products by distillation, the following are of interest with respect to the present invention.

German Auslegeschrift No. 1,295,543 and the priority case on which it is based, U.S. Pat. No. 3,282,801 (Wüst), issued Nov. 1, 1966 describe a process for the removal of TFE from mixtures formed in the pyrolysis of chlorodifluoromethane or bromodifluoromethane by extractive distillation with the addition of methanol, diethyl ether, acetone or ethyl acetate. According to the process of German Patent No. 1,161,877 and the priority case on which it is based, U.S. Pat. No. 3,101,304 (Wüst), issued Aug. 20, 1963, chlorinated hydrocarbons such as methylene chloride, chloroform, methyl chloride, carbon tetrachloride, dichloroethylene, trichloroethylene and tetrachloroethylene are used. These processes have the disadvantage that the boiling points of the extractants are very much higher than their temperature of use during the extractive distillation. As a result, substantial quantities of energy must be expended for the recovery, preparation in pure form and cooling before the extractants mentioned can be used, since the quantities to be used are large, especially if the extractive distillation is carried out using the main portion of the liquid pyrolysis condensate, such as is present in the bottom product of the first column. Likewise, comparatively larger and thus more expensive apparatuses such as heat-exchangers, distillation columns and the like are needed.

EP 38,970-A1 discloses a process by which the flue gas obtained after the condensation of the pyrolysis gases and containing nitrogen and carbon oxide is washed with difluoromonochloromethane, tetrafluoromonochloroethane or hexafluoromonochloropropane to recover the TFE contained therein. The TFE-containing wash liquid obtained is recycled into the liquefaction f the pyrolysis products. No mention is made of introducing this wash liquid at certain points during the purification process of the liquid pyrolysis products by distillation, which would be unwise anyway, since the wash liquid, in addition to TFE, contains undesired pyrolysis products which would interfere, if they did not run through the purification process from the beginning.

A process has now been found which makes it possible to produce pure TFE from pyrolysis gases by using a distillation aid having a low boiling point, which leads to a lower energy consumption and/or higher purity of the TFE produced and makes higher throughput quantities in the purification by distillation possible. If the pyrolysis product to be purified originates from the thermal decomposition of difluoromonochloromethane, the energy demand and expenditure in terms of apparatus is particularly small.

The novel process for the production of pure tetrafluoroethylene from a gas formed in the pyrolysis of a fluorocarbon compound having 1 to 4 carbon atoms, which can contain a hydrogen and a chlorine atom, which gas contains 20 to 70% by weight of tetrafluoroethylene after the removal of hydrogen chloride or hydrogen fluoride and if necessary of steam, by condensation of the gas under atmospheric or superatmospheric pressure, distillation of the liquid condensate in several columns connected in series, the compounds and azeotropic mixtures boiling at a lower temperature than tetrafluoroethylene being discharged at the top from the first column in the flow direction of the pyrolysis condensate and tetrafluoroethylene being discharged at the top from the second column in the flow direction of the condensate while the compounds and azeotropic mixtures boiling at a higher temperature than tetrafluoroethylene are discharged from the bottom of the second column and are worked up by distillation to produce further fluorocarbon compounds, which comprises introducing into the second column above the inlet for the bottom product of the first column 0.6 to 2 kg of difluoromonochloromethane per 1 kg of tetrafluoroethylene discharged from the second column.

Suitable fluorocarbon compounds for the preparation according to the invention of tetrafluoroethylene by pyrolysis are preferably the following: tetrafluoromonochloroethane, trifluoromethane and perfluorocyclobutane. Because of its favorable results, difluoromonochloromethane is particularly preferred as the feed product for the pyrolysis. It is also possible to use mixtures of the compounds mentioned as the feed product for the pyrolysis.

If the feed product for the pyrolysis contains bound hydrogen, hydrogen fluoride and/or hydrogen chloride is formed in the pyrolysis, depending on the type of compound or compound mixture used. Advantageously, these halides are removed, as already mentioned above, by dissolving them in water or in an aqueous solution which already contains hydrogen fluoride or hydrogen chloride. Advantageously, the pyrolysis gas which is then dried should contain 20 to 70% by weight, relative to the entire gas, of TFE. In principle, lower TFE contents are also possible, but the economy of the process then becomes worse without achieving the advantages. The treated pyrolysis gases described above which contain more than 70% by weight of tetrafluoroethylene usually require conditions of pyrolysis (for example high temperature) which favor the formation of undesirable by-products, thus worsen the yield, relative to the fluorocarbon compound used for the pyrolysis, and can lead to an unacceptably high expenditure in purification.

The condensation of the washed and dried pyrolysis gas is carried out at 0.1 to 1.5 MPa by cooling to the corresponding temperature. Preferably, the reaction s carried out in the pressure range from 0.15 to 0.5 MPa. The latter value should not be exceeded for reasons of safety (risk of explosion).

The portion of the pyrolysis gas liquefied by condensation is then distilled in a first distillation column, which, in order to obtain a sufficient separation effect, should have 30 to 150 theoretical plates, to separate the low-boiling components at the top. This column can be operated at a pressure from 0.3 to 1.8 MPa, preferably in the pressure range from 0.4 to 0.5 MPa, the upper value of the preferred range being determined, as already explained above, by safety considerations. The top product of the first column as well as the non-condensable flue gas from the pyrolysis are treated further by known methods to recover the comparatively low amounts of TFE contained therein. The bottom product of the first column is introduced into a second column, which should also have 30 to 150 theoretical plates to obtain a sufficient separation effect, and in this column pure TFE is distilled off at the top. The second column can be operated in the pressure range from 0.3 to 1.2 MPa, a range from 0.4 to 0.5 MPa also being preferred in this case for the reasons explained above.

According to the invention, 0.6 to 2 kg of difluoromonochloromethane per 1 kg of tetrafluoroethylene discharged from this second column are fed into this column above the inlet of the bottom product from the first column as distillation agent. Advantageously, the feeding level is selected such that the amount of difluoromonochloromethane mixing with the pure TFE is kept under 10 ppm (=parts of difluoromonochloromethane per 1 million parts of pure TFE), preferably under 5 ppm. If less than 0.6 kg of difluoromonochloromethane is used per kg of TFE, the effect according to the invention is no longer accomplished in columns of an industrially feasible number of plates. Although added amounts of more than 2 kg of difluoromonochloromethane per kg of TFE are possible, they do not result in any more additional advantages, but merely increase the costs; preferably, 0.75 to 1.5 kg of difluoromonochloromethane are used per kg of TFE.

By using the process according to the invention, only trifluoromethane and difluoroethylene have to be separated off completely in the first (low-boiling component) column, while the difluoromethane entered together with the pyrolysis gas condensate can be distributed between the top and bottom product. The lower demands on this separation make it possible to reduce the amount of reflux. 6 to 25 kg, preferably 6 to 15 kg, of top product of the first column are condensed per 1 kg of TFE discharged from the top of the second column and are recycled into the first column. Although a portion of the difluoromethane is introduced into the second (TFE) column together with the bottom product of the first column, this second column can also be operated at a comparatively low reflux ratio without risking the purity of the TFE produced because the difluoromethane is discharged from this column together with the bottom product. 3 to 10 kg, preferably 3 to 5 kg, of top product of the second column are condensed per 1 kg of tetrafluoroethylene discharged from the top of the second column and are recycled into this column, if the object is to produce TFE of ordinary purity. However, it is also possible to produce TFE of high purity in the recycling range from 5 to 10 kg of top product per kg of TFE produced, especially if a relatively large quantity, for example 1.5 to 2 kg, of difluoromonochloromethane per kg of TFE produced is fed into the second column.

The bottom product of the second (TFE) column is further worked up by distillation using known processes; advantageously, it is subjected to an extractive distillation to separate the azeotropic mixture consisting of difluoromonochloromethane and hexafluoropropene. For this purpose, known extractants such as methanol, acetone, diethyl ether or ethyl acetate can be used, substantially smaller amounts of extractants being used, and it being possible to work in a more favorable temperature range than if this extractive distillation, according to the state of the art, had been carried out using the entire pyrolysis gas.

A person skilled in the art could not have foreseen that, when using the process according to the invention, the separation effect of the second (TFE) column deteriorates, if the reflux ratio is chosen too high (significantly above 10 kg of top product per kg of TFE produced). In this respect, the separation according to the invention behaves contrary to what would be expected in an ordinary separation by distillation. The difference between the processes according to the invention and customary absorptive extractive distillations is that the distillation aid is only present in comparatively small proportions.

As already mentioned above, the process according to the invention makes it possible to prepare tetrafluoroethylene in good yield and purity at reduced costs in terms of energy and apparatus. Particularly advantageously, the novel process is used for the production of TFE from pyrolysis gases, generated by thermal decomposition of difluoromonochloromethane or substance mixtures which predominantly contain this substance.

The examples which follow are intended to illustrate the invention in more detail:

EXAMPLE 1

Gaseous difluoromonochloromethane is pyrolyzed in an electrically heated tube. The pyrolysis gases leave the tube at a temperature of 730° C., are then washed with an aqueous solution containing 30% by weight of hydrogen chloride, relative to the solution, and cooled with cooling water of 12° C., then passed through cooled water and then through dilute sodium hydroxide solution cooled to 12° C. and finally dried with concentrated sulfuric acid. After drying, the pyrolysis gases are condensed at −80° C. and the waste gas is discarded.

This gives 2,705 g/h of condensate having the following composition according to analysis by gas chromatograpy:

| | |
|---|---|
| difluoroethylene | 0.47 g/h |
| trifluoromethane | 4.19 g/h |
| tetrafluoroethylene | 1,025.21 g/h |
| difluoromethane | 0.30 g/h |
| trifluoroethylene | 0.83 g/h |
| difluoromonochloromethane | 1,095.81 g/h |
| remainder mainly consisting of hexafluoropropylene tetrafluoromonochloroethane perfluorocyclobutane and hexafluoromonochloropropane | 578.16 g/h |

This condensate is distilled at a pressure of 0.5 MPa in a first column, 25 mm in inner diameter,r filled with metal rings and having 84 theoretical plates, 6,700 g/h of the condensed top product being recycled into the column and 81.4 g/h of the top product being discharged. The top product discharged has the following composition according to analysis by gas chromatography:

| | |
|---|---|
| difluoroethylene | 0.47 g/h |
| trifluoromethane | 4.19 g/h |
| tetrafluoroethylene | 76.66 g/h |
| difluoromethane | 0.07 g/h |

It can be worked up by known purification processed for the purpose of producing tetrafluoroethylene.

The bottom product of the first column is again distilled at a pressure of 0.5 MPa in a second column, 25 mm in inner diameter, filled with metal rings and having 84 theoretical plates. Halfway up this column, 600 g/h of difluoromonochloromethane are introduced. The reflux is adjusted in such a manner that the top product does not contain more than 0.5 mg of each of difluoromethane or trifluoroethylene in 100 g of tetrafluoroethylene. This is achieved by recycling 3,300 g/h of the condensed top product into the second column and discharging 948.4 g/h of the top product. According to analysis by gas chromatography, it contains

| | |
|---|---|
| tetrafluoroethylene | 948.4 g/h |
| difluoromethane | 0.0047 g/h (<0.0005 g/100 g of TFE) |
| trifluoroethylene | <0.0005 g/h |

2,275.2 g of bottom product are discharged from the second column; according to analysis by gas chromatography, it has the following composition

| | |
|---|---|
| tetrafluoroethylene | 0.15 g/h |
| difluoromethane | 0.23 g/h |
| trifluoroethylene | 0.83 g/h |
| difluoromonochloromethane | 1,695.81 g/h |
| remainder mainly consisting of hexafluoropropylene tetrafluoromonochloroethane perfluorocyclobutane and hexafluoromonochloropropane | 578.16 g/h |

The bottom product can be subjected to further distillation stage for the purpose of producing difluoromonochloromethane, hexafluoropropylene and other products. The difluoromonochloromethane can be recovered by distillation in a temperature range which makes it possible to use steam as the heating source and water as the coolant, as a result of which only about 1/5 of the energy costs compared with the low temperature distillation f the substance mixtures containing tetrafluoroethylene have to be expended. The pyrolysis gas condensate obtained after separating off hydrogen chloride,e hydrogen fluoride after separating off hydrogen chloride,e hydrogen fluoride and steam contains 38.0% weight of tetrafluoroethylene. Per 1 kg of tetrafluoroethylene discharged from the second column there are:

0.63 kg of difluoromonochloromethane introduced into the second column, 7 kg of condensed top product of the first column recycled into this column and 3.5 kg of condensed top product of the second column recycled into this column.

COMPARATIVE TEST

The procedure as described in Example 1 is repeated, except that no difluoromonochloromethane is fed into the second column. The reflux ratio of the first and second column is again adjusted in such a manner that the top product of the second column does not contain more than 0.5 mg each of difluoromethane or trifluoroethylene per 100 g of tetrafluoroethylene. For this purpose, 18,100 g/h of condensed top product of the first column must be recycled into this column and 7,600 g/h of condensed top product of the second column must be recycled into the latter column. 80.2 g/h are discharged at the top of the first column.

| Composition: | |
|---|---|
| difluoroethylene | 0.57 g/h |
| trifluoromethane | 4.17 g/h |
| tetrafluoroethylene | 75.16 g/h |
| difluoromethane | 0.29 g/h |

953.7 g/h are discharged at the top of the second column.

| Composition: | |
|---|---|
| tetrafluoroethylene | 953.7 g/h |
| difluoromethane | 0.0048 g/h (0.0005 g/100 g of TFE) |
| trifluoroethylene | <0.0005 g/h |

1,676.1 g/h are discharged at the bottom of the second column.

| Composition: | |
|---|---|
| tetrafluoroethylene | 0.35 g/h |
| difluoromethane | 0.01 g/h |
| trifluoroethylene | 0.85 g/h |
| difluoromonochloromethane | 1,095.81 g/h |
| remainder mainly consisting of hexafluoropropylene tetrafluoromonochloroethane | |

| Composition: | |
|---|---|
| perfluorocyclobutane and hexafluoromonochloropropane | ~~579.1 g/h~~ |

The pyrolysis gas condensate contains 38.0% by weight of tetrafluoroethylene. Per 1 kg of tetrafluoroethylene discharged from the second column there are: 20 kg of condensed top product of the first column recycled into this column 8 kg of condensed top product of the second column recycled into this column. The energy required to be able to operate at much higher reflux ratios in the low temperature distillation in the first and second column in the comparative test than in the example according to the invention is substantial; in comparison, the saving of energy in the comparative test in which 600 g/h of difluoromonochloromethane less have to be recovered makes hardly any difference because its distillation can be carried out in a temperature range which is much more favorable energetically.

EXAMPLE 2

The procedure described in Example 1 is repeated with the following exceptions:

The second column has an inner diameter of 25 mm and is packed with metal rings, but is shorter and only has 63 theoretical plates. 1,140 g/h of difluoromonochloromethane are introduced halfway up the column. The reflux ratio of the first and second column is again adjusted in such a manner that the top product of the second column does not contain more than 0.5 mg each of difluoromethane or trifluoroethylene per 100 g of tetrafluoroethylene. For this purpose, 6,600 g/h of condensed top product of the first column must be recycled into this column and 3,800 g/h of condensed top part of the second column must be recycled into the latter column. 82.5 g/h are discharged at the top of the first column.

| Composition: | |
|---|---|
| difluoroethylene | 0.47 g/h |
| trifluoromethane | 4.19 g/h |
| tetrafluoroethylene | 77.76 g/h |
| difluoromethane | 0.07 g/h |

951.3 g/h are discharged at the top of the second column.

| Composition: | |
|---|---|
| tetrafluoroethylene | 951.3 g/h |
| difluoromethane | 0.0046 g/h (<0.0005 g/100 g of TFE) |
| trifluoroethylene | <0.0005 g/h |

2,812.3 g/h are discharged at the bottom of the second column.

| Composition: | |
|---|---|
| tetrafluoroethylene | 0.15 g/h |
| difluoromethane | 0.24 g/h |
| trifluoroethylene | 0.81 g/h |
| difluoromonochloromethane | 2,233.60 g/h |
| remainder mainly consisting of hexafluoropropylene | |
| tetrafluoromonochloroethane perfluorocyclobutane | 577.50 g/h |

| Composition: | |
|---|---|
| hexafluoromonochloropropane | |

The pyrolysis gas condensate contains 38.0% by weight of tetrafluoroethylene.

Per 1 kg of tetrafluoroethylene discharged from the second column there are:

1.2 kg of difluoromonochloromethane introduced into the second column 6.9 kg of condensed top product of the first column recycled into this column and 4 kg of condensed top product of the second column recycled into this column.

We claim:

1. In a process for the production of pure tetrafluoroethylene from the gaseous pyrolysis products of a pyrolyzable $C_1$ to $C_4$ fluorocarbon which is pyrolyzable to form tetrafluoroethylene, said gaseous pyrolysis products comprising 20 to 70 percent by weight of tetrafluoroethylene and being essentially dry and essentially freed of any hydrogen chloride or hydrogen fluoride, condensing said pyrolysis gas to obtain a liquefied portion of the gas, introducing this liquefied portion of the gas into a first distillation column and separating by distillation at the top end of this column as a top product of the first column components boiling at a lower temperature than does tetrafluoroethylene, thereby forming a bottom product of the first distillation column and introducing this bottom product through an inlet into a second distillation column, distilling off pure tetrafluoroethylene as a top product of the second distillation column and discharging at the bottom of said column components boiling at a higher temperature than does tetrafluoroethylene, the improvement which comprises introducing into the second distillation column above the inlet for the bottom product of the first distillation column 0.6 to 2 kg of difluoromonochloromethane per 1 kg of tetrafluoroethylene discharged from the top of the second distillation column above the inlet for the bottom product of the first distillation column 0.6 to 2 kg of difluoromonochloromethane per 1 kg of tetrafluoroethylene discharged from the top of the second distillation column.

2. The process as claimed in claim 1, wherein 3 to 5 kg of the top product of the second distillation column per 1 kg of tetrafluoroethylene discharged at the top of the second distillation column are condensed and recycled into this column.

3. The process as claimed in claim 1, wherein 6 to 15 kg of the top product of the first distillation column per 1 kg of tetrafluoroethylene discharged from the top of the second distillation column are condensed and recycled into the first distillation column.

4. The process as claimed in claim 1, wherein the first and second distillation columns are operated in the pressure range from 0.4 to 0.5 MPa.

5. The process as claimed in claim 1, wherein the compound pyrolyzed is difluoromonochloromethane.

6. The process as claimed in claim 1, wherein the $C_1$ to $C_4$ fluorocarbon is difluoromonochloromethane, tetrafluoromonochloroethane, trifluoromethane, perfluorocyclobutane or a mixture thereof.

7. The process as claimed in claim 1, wherein the components discharged at the bottom of the second distillation column are processed to recover additional fluorocarbon compounds.

8. A process for the production of pure tetrafluoroethylene from the gaseous pyrolysis products of a $C_1$ to $C_4$ fluorocarbon which is pyrolyzable to form a gas containing 20 to 70 weight-% tetrafluoroethylene, said gas being condensable to form a liquefied portion comprising tetrafluoroethylene, high-boiling constituents having a boiling temperature higher than that of tetrafluoroethylene, and low-boiling constituents having a boiling temperature lower than that of tetrafluoroethylene, said process comprising:

condensing said gas to form said liquefied portion, introducing said liquefied portion into a first distillation column and separating by distillation at the top of the this column said high-boiling constituents while removing as a bottom product tetrafluoroethylene and said low-boiling constituents from the bottom of this column, introducing said bottom product into a second distillation column and distilling off pure tetrafluoroethylene as a top product of the second distillation column, and introducing into the second distillation column above the inlet for the bottom product of the first column 0.6 to 2 kg of difluoromonochloromethane per 1 kg of tetrafluoroethylene discharged from the top of the second column.

* * * * *